United States Patent [19]
Descamps et al.

[11] Patent Number: 5,780,666
[45] Date of Patent: Jul. 14, 1998

[54] PROCESS FOR THE PREPARATION OF AN OPTICALLY PURE AMINOALCOHOL

[75] Inventors: Marcel Descamps, Lherm; Joël Radisson, Saubens; Anne-Archard Gilles, Toulouse, all of France

[73] Assignee: Sanofi, Paris, France

[21] Appl. No.: 598,001

[22] Filed: Feb. 7, 1996

Related U.S. Application Data

[60] Division of Ser. No. 294,035, Aug. 24, 1994, Pat. No. 5,512,680, which is a continuation-in-part of Ser. No. 202,027, Feb. 25, 1994, abandoned.

[30] Foreign Application Priority Data

Feb. 25, 1993 [FR] France .................................. 93 02262

[51] Int. Cl.$^6$ ............................................ C07C 255/19
[52] U.S. Cl. ............................................ 558/406
[58] Field of Search ............................................ 558/406

[56] References Cited

PUBLICATIONS

Cheng, C.Y. et al, Zhonghua Yaoxue Zazhi, 1992, 44(1), pp. 45–50.

*Primary Examiner*—C. Warren Ivy
*Assistant Examiner*—Garth M. Dahlen
*Attorney, Agent, or Firm*—Bacon & Thomas

[57] ABSTRACT

A process is described for the preparation of (+)-2-(3,4-dichlorophenyl)-4-hydroxybutylamine (I) by reaction of 3,4-dichlorophenylacetic acid (II) with an alkali metal halogenoacetate, treatment of the 3-cyano-3-(3,4-dichlorophenyl)propionic acid (III) with D-(−)-N-methylglucamine, with second-order asymmetric conversion, hydrolysis of the D-(−)-N-methylglucamine salt of (−)-3-cyano-3-(3,4-dichlorophenyl)propionic acid and enantioconservative reduction of the resulting levorotatory cyanoacid with a borane.

1 Claim, No Drawings

PROCESS FOR THE PREPARATION OF AN OPTICALLY PURE AMINOALCOHOL

This application is a Division of application Ser. No. 08/294,035, filed Aug. 24, 1994, now U.S. Pat. No. 5,512,680, which is a continuation-in-part of application Ser. No. 08/202,027, filed Feb. 25, 1994, now abandoned.

The present invention relates to a process for the preparation of dextrorotatory 2-(3,4-dichlorophenyl)-4-hydroxybutylamine of the formula

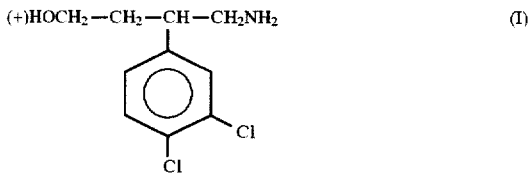

The compound (I) is a key intermediate in the synthesis of tachykinin antagonists. The compound (I) is described in the U.S. patent application Ser. Nos. 07/610,093(granted under No.5,317,020), 08/208,672, 07/755,454 (granted under No.5,236,921), 07/877,734, 08/026,154 and 08/129,311 which are incorporated herein by reference.

According to the above document, the compound (I) is prepared by resolving the racemate via its D-(−)-tartrate.

It has now been found that treating racemic 3-cyano-3-(3,4-dichlorophenyl)propionic acid with D-(−)-N-methylglucamine effects a second-order asymmetric conversion to give (−)-3-cyano-3-(3,4-dichlorophenyl)-propionic acid, which, on enantioconservative reduction with a borane, gives the compound (I).

It has also been found, surprisingly, that the compound of formula (I) can be obtained from 3,4-dichlorophenylacetonitrile by reaction with an alkali metal halogenoacetate, preferably sodium chloroacetate, resolution of the 3-cyano-3-(3,4-dichlorophenyl)propionic acid in situ and enantioconservative reduction as indicated above.

Thus, according to one of its features, the present invention relates to a process for the preparation of (+)-2-(3,4-dichlorophenyl)-4-hydroxybutylamine of formula (I), which comprises (a) treating 3,4-dichlorophenylacetonitrile of formula (II):

with an alkali metal halogenoacetate in liquid ammonia or in a polar aprotic solvent, in the presence of a strong base, at a temperature of −40° C. to +25° C.;

(b) treating the resulting racemic 3-cyano-3-(3,4-dichlorophenyl)propionic acid of formula (III):

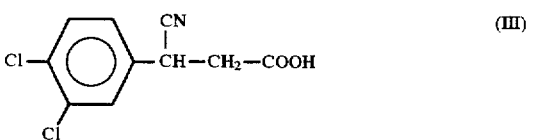

with D-(−)-N-methylglucamine in order to crystallize all the acid (III) in the form of the D-(−)-N-methylglucamine salt of the levorotatory acid;

(c) treating said salt with a strong acid; and (d) subjecting the freed (−)-3-cyano-3-(3,4-dichlorophenyl)propionic acid of formula (IV):

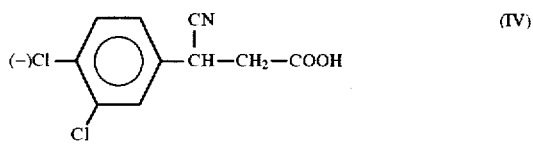

to enantioconservative reduction with a borane to give the derivative (I).

More particularly, step (a) is carried out using an alkali metal halogenoacetate such as sodium or potassium chloroacetate or sodium or potassium bromoacetate, in the presence of a strong base such as sodium amide, sodium tert-butylate or sodium ethylate. Solvents which can be used are liquid ammonia at low temperature (−40° C. to −30° C.) or a polar aprotic solvent which is inert under the reaction conditions, such as dimethyl sulfoxide or N,N-dimethylformamide. The cyanoacid of formula (III) thus obtained after a reaction time of 4–5 hours is isolated by treatment with water or mixtures of water with an ether, for example isopropyl ether. It can be converted to one of its salts.

Step (b) can be carried out on the isolated cyanoacid (III) or else in situ directly after step (a) in a solvent such as an alcohol, preferably ethanol. The D-(−)-glucamine salt of (−)-3-cyano-3-(3,4-dichlorophenyl)propionic acid crystallizes directly and can be isolated.

The levorotatory acid is freed from its salt by treatment with a strong acid, according to step (c), and isolated by extraction with an appropriate solvent such as dichloromethane, dichloroethane or 1,1,1-trichloroethane. The acid (IV) can be converted to one of its salts.

In step (d), the enantioconservative reduction with a borane such as BH$_3$ or B$_2$H$_6$, optionally in the form of a complex with tetrahydrofuran or dimethyl sulfide, is carried out at room temperature in a solvent of the ether type, such as dioxane or tetrahydrofuran. After the excess borane has been destroyed and the solvent has been evaporated off, the aminoalcohol (I) is isolated by removal of the by-products using successive treatments with an acid and then with a base, followed by extraction with an appropriate solvent such as dichloromethane, dichloroethane or 1,1,1-trichloroethane.

3-Cyano-3-(3,4-dichlorophenyl) propionic acid (III) is prepared by reacting sodium chloroacetate with 3,4-dichlorophenylacetonitrile (II), for example in liquid ammonia in the presence of sodium amide according to the technique of A. G. CHIGAREV and D. V. IOFFE, Zh. Org. Khim. 3, 85–8 (1967), or in the presence of another very strong base such as sodium or potassium tert-butylate in liquid ammonia at −33° C. or in anhydrous dimethyl sulfoxide at room temperature. The yield of 3-cyano-3-(3,4-dichlorophenyl)propionic acid isolated is 74 to 78%, but it is even better if the product is not isolated, because it suffices to react it with D-(−)-N-methylglucamine, an inexpensive industrial product obtained from D-glucose and methylamine (KARRER, HERKENRATH—Helv. Chim. Acta, 20, 37 (1937)), in order to crystallize all the racemic cyanoacid (III) in the form of the salt of the levorotatory acid. The yield is excellent, being 190% based on the levorotatory enantiomer contained in the racemate (III). The crystallization solvent can be methanol, ethanol, Cellosolve® or any other suitable solvent. The resolution temperature is between the boiling point of the solvent and 0° C. The N-methylglucamine must be present in at least the stoichiometric amount. It is preferably used in slight excess.

After the 3-cyano-3-(3,4-dichlorophenyl)propionic acid has been freed from its D-(−)-N-methyl-glucamine salt by reaction with a strong acid such as hydrochloric acid, oxalic acid or an ion exchange resin of the sulfonic acid type, it is reduced in an enantioconservative manner (enantiomeric purity: 99%) with borane.

The yield of this double reduction is at least 70%.

The borane can be used in the form of its dimer, $B_2H_6$, but is preferably used in a more manipulable form such as the complex form with tetrahydrofuran or dimethyl sulfide, the latter complex being marketed as BMS.

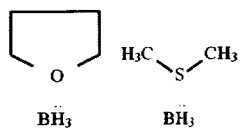

The second-order asymmetric conversion according to step (b) of the process of the present invention is surprising and constitutes a further subject of the present invention, which thus relates, according to another of its features, to a process for the preparation of (−)-3-cyano-3-(3,4-dichlorophenyl)propionic acid, which comprises treating racemic 3-cyano-3-(3,4-dichlorophenyl)propionic acid with D-(−)-N-methylglucamine and treating the resulting D-(−)-N-methylglucamine salt of (−)-3-cyano-3-(3,4-dichlorophenyl)-propionic acid with a strong acid.

3-Cyano-3-(3,4-dichlorophenyl)propionic acid (III) and its salts, and its (−) isomer of formula (IV) and its salts, are novel products and represent a further feature of the present invention.

More particularly, the D-(−)-N-methylglucamine salt of (−)-3-cyano-3-(3,4-dichlorophenyl)propionic acid constitutes another feature of the present invention.

The compound (I) as obtained by the process according to the invention may advantageously be used for the stereoselective synthesis of optically pure arylalkylamines, which are antagonists of neurokinin receptors.

Particularly, the compound (I) may be used for the preparation of the arylalkylamines described in the U.S. patent application Ser. Nos. 07/610,093 (granted under No.5,317,020), 08/208,672, 07/755,454 (granted under No.5,236,921), 07/877,734, 08/026,154 and 08/129,311 according to the general scheme illustrated below in Scheme 1, in which the substituents B and D represent all the substituents of the aminated ring of the arylalkylamines described in the U.S. patent applications referred above, W, T and Z are as described in said patent applications, and Ar' is a dichlorophenyl group.

SCHEME 1

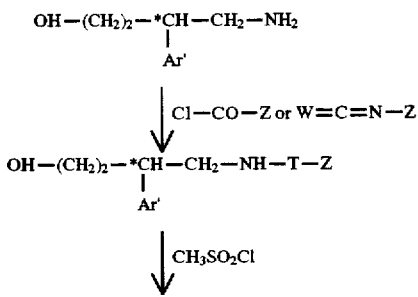

-continued
SCHEME 1

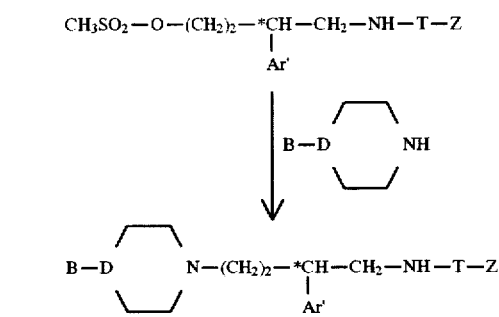

The sign "*" means that the carbon atom identified by this symbol has the defined configuration (+) or (−).

Preferably, the compound (I) as obtained by the process of the invention will be used for the preparation of optically pure arylalkylamines of formula (VI)

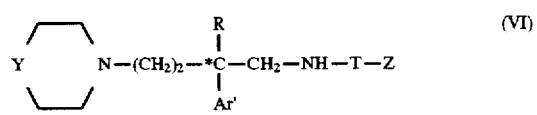

in which

Y represents—either a group Cy—N in which

Cy represents a phenyl, unsubstituted or substituted one or more times with one of the substituents selected from:

hydrogen, a halogen atom, a hydroxyl, a $C_1$–$C_4$ alkoxy, a $C_1$–$C_4$ alkyl, a trifluoromethyl, the said substituents being the same or different; a $C_3$–$C_7$ cycloalkyl group; a pyrimidinyl group or a pyridyl group;

or a group

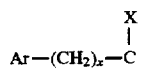

in which

Ar represents a phenyl, unsubstituted or substituted one or more times with one of the substituents selected from:

hydrogen, a halogen atom, a hydroxyl, a $C_1$–$C_4$ alkoxy, a $C_1$–$C_4$ alkyl, a trifluoromethyl, the said substituents being the same or different; a pyridyl group; a thienyl group;

x is 0 or 1;

X represents a hydroxyl, a $C_1$–$C_4$ alkoxy; a hydroxyalkyl in which the alkyl group is a $C_1$–$C_3$ alkyl group; a $C_1$–$C_4$ acyloxy; a phenacyloxy; a carboxyl, a $C_1$–$C_4$ carbalkoxy; a cyano; an aminoalkylene in which the alkylene is a $C_1$–$C_3$ group; a group —N—$(X_1)_2$ in which the groups $X_1$ independently represent hydrogen, a $C_1$–$C_4$ alkyl; a group —NH—CO—Alk in which Alk represents a $C_1$–$C_6$ alkyl;

a group $Alk_1$—NH—CO—$Alk'_1$ in which $Alk_1$ is a $C_1$–$C_3$ alkylene and $Alk'_1$ is a $C_1$–$C_3$ alkyl; a $C_1$–$C_4$ acyl; a group —S—$X_2$ in which $X_2$ represents hydrogen or a $C_1$–$C_4$ alkyl group;

or alternatively, X forms a double bond with the carbon atom to which it is linked and with the adjacent carbon atom in the heterocycle;

Ar' represents a dichlorophenyl group;

R represents hydrogen;

T represents a group selected from

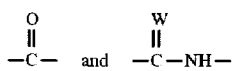

W being an oxygen or a sulphur atom, and
Z represents either hydrogen, or M or OM when T represents a

group, or M when T represents a group

M represents a $C_1$–$C_6$ alkyl; a phenylalkyl in which the alkyl is a $C_1$–$C_3$ group, optionally substituted on the aromatic ring with a halogen, a trifluoromethyl, a $C_1$–$C_4$ alkyl, a hydroxyl, a $C_1$–$C_4$ alkoxy; a pyridylalkyl in which the alkyl is a $C_1$–$C_3$ group; a naphthylalkyl group, optionally substituted on the naphthyl ring with a halogen, a trifluoromethyl, a $C_1$–$C_4$ alkyl, a hydroxyl, a $C_1$–$C_4$ alkoxy; a pyridylthioalkyl in which the alkyl is a $C_1$–$C_3$ group; a styryl; an optionally substituted mono-, di- or tricyclic aromatic or heteroaromatic group;
or of one its salts with inorganic or organic acids.

The compounds of formula (VI), which are described in the U.S. Pat. No. 5,236,921, are prepared according to the above Scheme 1, in which B-D< is represented in formula (VI) by Y.

The compound of formula (I) obtained by the process according to the invention is particularly suitable for the preparation of the (−)-N-methyl-N-[4-(4-phenyl-4-acetylamino-piperidyl)-2-(3,4-dichlorophenyl)butyl] benzamide or pharmaceutically acceptable salts thereof, such as hydrochloride or methanesulfonate.

Thus, a further object of the invention is a process for preparing the (−)-N-methyl-N-[4-(4-phenyl-4-acetylamino-piperidyl)-2-(3,4-dichloro-phenyl)butyl]-benzamide and its pharmaceutically acceptable salts which comprises:

(a) reacting a compound of formula (I)

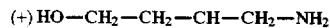

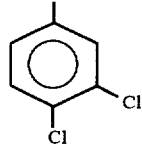

with a functional derivative of benzoic acid,
(b) reacting the (+)-N-[2-(3,4-dichlorophenyl-4-hydroxy) butyl]benzamide thus obtained of formula (VIII)

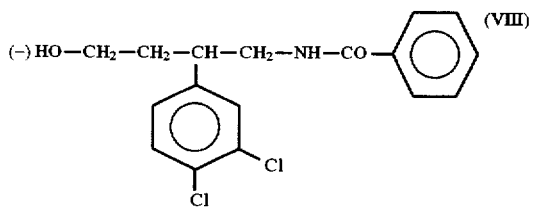

with dihydropyrane, (c) reacting the O-protected compound thus obtained of formula (IX)

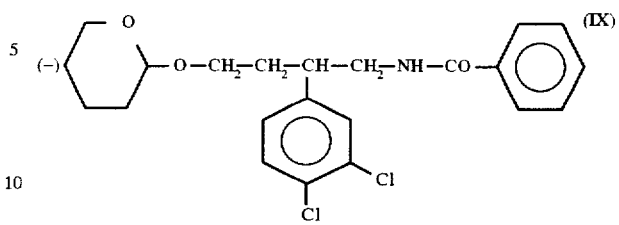

with dimethylsulfate,
(d) O-deprotecting the compound thus obtained of formula (X)

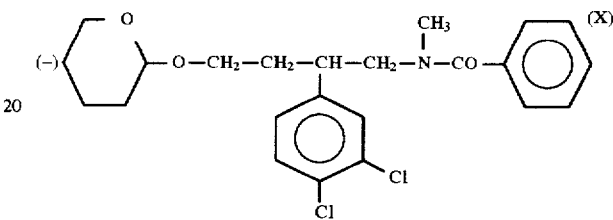

in an acidic medium,
(e) treating compound thus obtained of formula (XI)

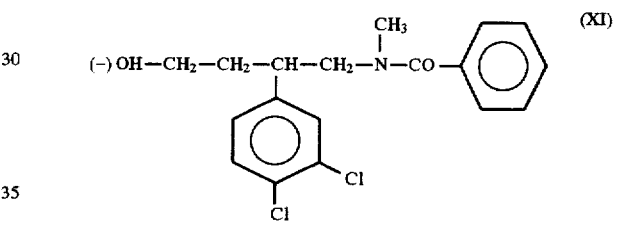

with a functional derivative of benzenesulfonic acid,
(f) reacting the benzenesulfonate thus obtained of formula (XII)

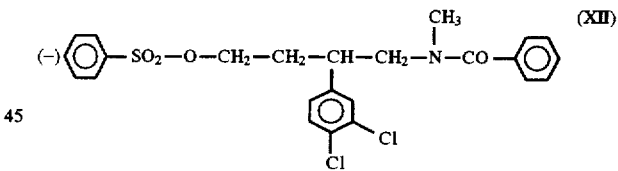

with 4-acetylamino-4-phenylpipiridine, and
(g) isolating the (−)-N-methyl-N-[4-(4-phenyl-4-acetylaminopiperidyl)-2-(3,4-dichloro-phenyl)butyl]-benzamide as such, or if desired, converting it to one of its pharmaceutically acceptable salts.

The functional derivative of benzoic acid used in step (a) may be the acid itself, activated for example with dicyclohexylcarbodiimide, its chloride, its anhydride, a mixed anhydride or an active ester.

In step (b), the O-protection may be carried out in the presence of an acid, for example methanesulfonic acid.

In step (c) the reaction with dimethyl sulfate is carried out in the presence of sodium hydride in a polar aprotic solvent such as dimethylformamide.

The O-deprotection of step (d) may be carried out, in an acidic medium, using for example hydrochloric or methane sulfonic acid, or also a $H^+$ resin such as AMBERLIST® 15, in methanol.

As functional derivative of benzenesulfonic acid, its chloride is preferably used in step (e).

In step (f) the reaction of compound (IX) with 4-acetylamino-4-phenylpiperidine is carried out, preferably, in a polar aprotic solvent such as dimethylacetamide, dimethylformamide or acetonitrile in the presence of a base such as sodium or potassium carbonate, triethylamine or 4-dimethylaminopyridine.

The (−)-N-methyl-N-|4-phenyl-4-acetylaminopiperidin-1-yl)-2-(3,4-dichlorophenyl)-butyl|benzamide thus obtained is isolated in form of free base or of one of its salts, for example the hydrochloride, the fumarate or the succinate. It is also possible to isolate the product for example as a fumarate salt and converting it in another salt by previously neutralizing it and treating the free base with an acid, for example succinic acid.

According to this process, it is possible to combine two or more steps to carry out them in one pot. For example, steps (a) and (b) may be combined in order to obtain compound (VIII) directly starting from compound (I).

Analogously, N-methylation and O-deprotection of steps (c) and (d) may be combined and compound (X) may be obtained without isolating (IX).

Also the final steps (e), (f) and (g) may be combined.

Other combinations of more than two steps may be envisaged and it is also possible to carry out the whole process in one pot.

The compounds of formula (I), as obtained by the process of the invention may also be used for the preparation of optically pure arylalkylamines of formula (VII)

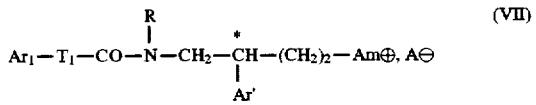
(VII)

in which

Ar₁ is an optionally substituted mono-, di- or tri-cyclic aromatic or heteroaromatic group;

T₁ is a direct bond, a hydroxymethylene group, an alkoxymethylene group in which the alkoxy group is $C_1-C_4$, or a $C_1-C_5$ alkylene group;

Ar' is a dichlorophenyl group;

R is hydrogen;

Am⊕ is the radical

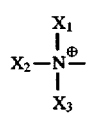

in which $X_1$, $X_2$ and $X_3$, together with the nitrogen atom to which they are bonded, form an azabicyclic or azatricyclic system optionally substituted by a phenyl group; and A⊖ is a pharmaceutically acceptable anion.

The compounds of formula (VII), which are described in the U.S. patent application Ser. No. 08/129,311, are prepared by a process consisting essentially in:

reacting a compound of formula (I) as obtained by the process of the invention with a compound of formula

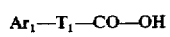
Ar₁—T₁—CO—OH in which T₁ and Ar₁ are as defined above, and reacting the resulting compound, of formula

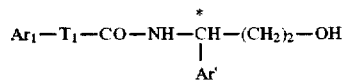

in which Ar' is as defined above, with a compound of formula G—Cl, in which G is a leaving group such as mesyl or benzene sulfonyl, then reacting the resulting compound, of formula

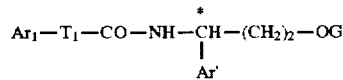

with a tertiary amine of formula

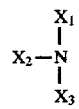

in which $X_1$, $X_2$ and $X_3$ are as defined above, in an organic solvent at a temperature between ambient and 120° C., and isolating the resulting product or else, if appropriate, exchanging the methane sulfonate anion of the resulting quaternary salt with another pharmaceutically acceptable anion.

The compound of formula (I) as obtained according to the process of the invention is particularly suitable for the preparation of the (+)-1-|2-|3-3,4-dichlorophenyl-1-|(3-isopropoxyphenyl)-acetyl|piperidyn-3-yl|ethyl|-4-phenyl-1-azonia-bicyclo-|2.2.2|octane chloride.

The Examples which follow illustrate the invention without however implying a limitation.

EXAMPLE 1

(±)-3-Cyano-3-(3,4-dichlorophenyl)propionic acid (III)

A mixture of 18.6 g (0.10 mol) of 3,4-dichlorophenylacetonitrile and 12 g (1.03 mol) of dry sodium chloroacetate is reacted for 5 hours at room temperature in 150 ml of dry dimethyl sulfoxide, in the presence of 10.5 g (1.05 mol) of sodium tert-butylate. After the reaction, the reaction mixture is poured into 1 liter of iced water and acidified to pH<3 with hydrochloric acid. The cyanoacid is extracted with ethyl acetate, which is washed to pH>3, dried over magnesium sulfate and concentrated to dryness. The residue is solidified in 1,2-dichloroethane to give 16.1 g of the expected compound (III), which is characterized by proton NMR.

EXAMPLE 2

(±)-3-Cyano-3-(3,4-dichlorophenyl)propionic acid (III)

A mixture of 93 g (0.50 mol) of 3,4-dichlorophenylacetonitrile and 64 g (0.55 mol) of sodium chloroacetate is reacted for 4 hours at −33° C. in 500 ml of liquid ammonia, in the presence of 21 g (0.54 mol) of sodium amide. After evaporation of the ammonia, the residue is taken up with water and then with isopropyl ether and is acidified to pH<3 with hydrochloric acid. The organic phase is washed with water to pH>3, separated off by decantation, dried over magnesium sulfate and concentrated to dryness. The residue is solidified in toluene and characterized by proton NMR. M.p.=106° C.

EXAMPLE 3

(±)-3-Cyano-3-(3,4-dichlorophenyl)propionic acid (III)

A mixture of 186 g (1.00 mol) of 3,4-dichlorophenylacetonitrile and 126 g (1.05 mol) of sodium tert-butylate is reacted for 4 hours at −33° C. in 1 liter of liquid ammonia. After the reaction, the ammonia is evaporated off and the residue is taken up with 500 ml of iced water and then with 500 ml of isopropyl ether and is acidified to pH<3 with hydrochloric acid. The aqueous phase is discarded and the organic phase is washed with water to pH>3, separated off by decantation, dried over magnesium sulfate and concentrated under vacuum. The residue is solidified in 250 ml of toluene and the cyanoacid is filtered off and dried at 50° C. under a vane pump vacuum to give 190 g (yield: 78%) of the expected (±)-3-cyano-3-(3,4-dichloro phenyl)propionic acid. M.p.=104° C.

The product is characterized by proton NMR at 200 MHz in DMSO:

unresolved signals between 2.85 and 3.1 ppm, 2 protons: —CH$_2$— complex signal at 4.5 ppm, 1 proton: —CH— aromatic, protons between 7.4 and 7.75 ppm, 3 protons one acidic proton at 12.8 ppm

EXAMPLE 4

(−)-3-Cyano-3-(3,4-dichlorophenyl)propionic acid (IV)

A mixture of 186 g (1.00 mol) of 3,4-dichlorophenylacetonitrile, 126 g (1.05 mol) of sodium chloroacetate and 105 g (1.05 mol) of sodium tert-butylate is reacted for 4 hours at −33° C. in 1 liter of liquid ammonia.

After the reaction, the ammonia is evaporated off and the residue is taken up with 500 ml of iced water and then with 500 ml of isopropyl ether and is acidified to pH<3 with hydrochloric acid. The aqueous phase is discarded and the organic phase is washed with water to pH>3, separated off by decantation, dried over magnesium sulfate and concentrated under vacuum. The concentrate is redissolved in 2 liters of absolute ethanol, the solution is heated and 292 g of D-(−)-N-methylglucamine are added. After crystallization, the product is filtered off, rinsed with ethanol and dried under vacuum to give 396 g of the N-methylglucamine salt of (−)-3-cyano-3-(3,4-dichlorophenyl)propionic acid. $[\alpha]_D^{25}$=14.7° (C=1, CH$_3$OH).

The yield is 91% based on the 3,4-dichlorophenylacetonitrile.

The salt obtained is dissolved in 900 ml of 1N hydrochloric acid and extracted with 2 liters of dichloromethane. The organic phase is washed with water, separated off by decantation, dried over sodium sulfate and concentrated. The product is solidified in 500 ml of cyclohexane to give 187 g of the expected product. The yield is 76.5% based on the 3,4-dichlorophenylacetonitrile. M.p.=98° C. $[\alpha]_D^{25}$=8.6° (C=1, CH$_3$OH). Enantiomeric purity by HPLC: 99%. Proton NMR at 200 MHz in DMSO: same spectrum as the racemate.

EXAMPLE 5

(+)-2-Cyano-3-(3,4-dichlorophenyl)-4-hydroxy butylamine (I)

350 ml of a 1 molar solution of BH$_3$ in THF are added to a solution of 244 g (1 mol) of (−)-3-cyano-3-(3,4-dichlorophenyl)propionic acid in 500 ml of THF, cooled to 0° C. When the evolution of hydrogen has ceased, 650 ml of the borane solution are added at 20° C., followed by 1000 ml at 40° C. When the reaction is complete, the excess borane is destroyed by the addition of methanol and the reaction mixture is concentrated to dryness. The concentrate is dissolved in 500 ml of water, acidified with hydrochloric acid and washed twice with 250 ml of toluene. The aqueous phase is rendered alkaline with sodium hydroxide and extracted with twice 400 ml of dichloromethane. The organic phase is washed with water, separated off by decantation, dried over magnesium sulfate and concentrated under vacuum to give 159 g (yield: 68%) of the expected product. Chiral purity by HPLC: 99%.

The product is characterized by proton NMR in CDCl$_3$ at 200 MHz:

unresolved signals at 1.8 ppm, 2H one singlet at 2.4 ppm, 3H unresolved signals between 2.65 and 2.9 ppm, 3H unresolved signals between 3.35 and 3.6 ppm, 2H aromatic protons between 6.95 and 7.35 ppm, 3H $[\alpha]_D^{25}$=+9.8° (C=1, MeOH). M.p.=80°–81° C.

EXAMPLE 6

(+)-2-(3,4-Dichlorophenyl)-2-hydroxybutylamine (I)

The procedure of EXAMPLE 5 is followed except that borane dimethyl sulfide is used, dilution is carried out with 750 ml of tetrahydrofuran and the operating temperatures are 20° C. and then 50° C. The same product is obtained with the same yield and the same characteristics.

EXAMPLE 7

(−)-N-methyl-N-[4-(4-phenyl-4-acetylaminopiperidyl)-2-(3,4-dichloro-phenyl)butyl]-benzamide (a) To a solution of 5.85 kg of (+)a-2-(3,4-dichlorophenyl)-4-hydroxybutylamine (I) and 3.0 kg of triethylamine in 25 ml of dichloromethane there are added 3.52 kg of benzoyl chloride, dissolved in 15 l of dichloromethane, at a temperature lower than 15° C. The mixture is treated with 20 l of ice-water, then the aqueous phase is decanted, extracted with 10 l of dichloromethane and eliminated. The collected organic phases are collected, washed with 5% hydrochloric acid, then with a 5% aqueous solution of sodium bicarbonate, with water and dried over sodium sulfate.

b) To the solution thus obtained, containing compound (VIII), 2.5 kg of dihydropyrane, 10 g of methanesulfonic acid are added and it is stirred 3 hours at room temperature (about 22° C.). When the reaction is over, the reaction mixture is concentrated, the concentrate is dissolved in 30 l of isopropyl ether and let to crystallize. Compound (IX) thus obtained is filtered, washed with isopropyl ether and dried under vacuum. Yield: 85% from (I).

c) A solution of 6.8 g of (IX) in 10 l of dimethylformamide are added to a suspension of 0.90 kg of 60% sodium hydride in 5 l of dimethylformamide. When hydrogen has ceased to develop, 3.3 kg of dimethylsulfate in 5 l of toluene are added thereto. After one hour, 45 l of water and, afterwards, sodium hydroxide are added to a pH higher than 6. The solution is extracted twice with 25 l of the chloromethane and the aqueous phase is eliminated. The organic layer is washed with water to pH 7 and concentrated.

(d) The above concentrate containing compound (X) is dissolved in 25 l of methanol and 0.5 kg of Amberlist® 15 is added thereto. The mixture is stirred 3 hours at 20° C.–30° C. Then the resine is filtered, washed with 5 l of methanol and the filtrate is concentrated. The residue is taken up with 25 l of toluene and let to crystallize. Compound (XI) thus obtained is filtered, washed with 5 l of toluene and dried under vacuum. Yield: 85° from (IX).

(e) To a solution of 7.06 kg of compound (XI) and 2.70 kg of triethylamine in 25 l of toluene at 60° C., 7.06 g of benzenesulfonylchloride are added. The reaction mixture is heated at 65° C. over 15 minutes, then 3 hours at 45° C. When the reaction is over, the mixture is cooled to 10° C. then 20 l of water are added thereto. The mixture is stirred 5 minutes, then decanted and the aqueous phase is eliminated. The organic phase is stirred with 20 l of water containing 6.2 l of a solution of 400 g/l sodium hydroxide until the total hydrolysis of the exces of benzenesulfonylchloride (3 hours at room temperature) occurs. Then the aqueous phase is eliminated, the organic phase is dried over sodium sulfate and concentrated under vacuum. The concentrate contains compound (XII), obtained in a 80–100% yield.

(f) and (g) A portion of the concentrate obtained in step (e) corresponding to 4.93 kg (±200 g) calculated by HPLC, and 2.20 kg of 4-acetylamino-4-phenylpiperidine in acetonitrile are refluxed in the presence of 2 kg of potassium carbonate. When the reaction is over, the mixture is concentrated under vacuum, the residue is taken up with 50 l of water and 20 l of dichloromethane. The mixture is stirred 5 minutes and decanted. The aqueous phase is extracted with 5 l of dichloromethane and eliminated. The collected organic phases are washed twice with 50 l of 3N hydrochloric acid, then twice with 25 l of water, then once with 25 l of 2N sodium hydroxide and finally with water until a pH lower than 10. After drying over sodium sulfate, the solvent is distilled off under vacuum, the residue is taken up with 25 l of acetone and the solution is added to a suspension of 1.275 kg of fumaric acid in 25 l of acetone at reflux. The mixture is let to cool at room temperature and the (−)-N-methyl-N-|4-(4-acetylamino-4-phenylpiperidin-1-yl)-2-(3,4-dichlorophenyl)butyl|benzamide monofumarate is filtered, washed with acetone and dried under vacuum. Yield 80%.

A mixture of 6.68 kg of the product thus obtained in 30 l of dichloromethane and 20 l of water is made basic under stirring by addition of 2.5 l of an aqueous solution containing 400 g/l of sodium hydroxide. After 25 minutes of stirring, the reaction mixture is decanted, the aqueous phase is extracted with 10 l of dichloromethane and eliminated. The organic phases are collected, washed with water to a pH lower than 8, dried over sodium sulfate and concentrated under vacuum. Thus the (−)-N-methyl-N-|4-(4-acetylamino-4-phenylpiperidin-1-yl)-2-(3,4-dichlorophenyl)butyl|benzamide base is obtained.

The base thus obtained is dissolved in 15 l of acetone and the solution is poured into a solution of 1.24 kg of succinic acid in 25 l of acetone. After cooling, the (−)-N-methyl-N-|4-(4-acetylamino-4-phenylpiperidin-1-yl)-2-(3,4-dichlorophenyl)butyl|-benzamide monosuccinate thus obtained is filtered, washed with 10 l of acetone and dried under vacuum at 50° C., m.p., Yield: 90%.

What is claimed is:

1. (−)-3-Cyano-3-(3,4-dichlorophenyl)propionic acid or its salts, substantially free of its (+) enantiomer.

* * * * *